United States Patent

(12) United States Patent
Weston et al.

(10) Patent No.: US 6,509,516 B1
(45) Date of Patent: Jan. 21, 2003

(54) MALE-STERILE BRASSICA PLANTS AND METHODS FOR PRODUCING SAME

(75) Inventors: Brigitte Weston, Aalter (BE); Marc de Beuckeleer, Ghent (BE)

(73) Assignee: Plant Genetic Systems N.V., Ghent (BE)

( * ) Notice: Subject to any disclaimer, the term of this patent is extended or adjusted under 35 U.S.C. 154(b) by 0 days.

(21) Appl. No.: 09/430,497

(22) Filed: Oct. 29, 1999

(51) Int. Cl.$^7$ .......................... A01H 5/00; A01H 5/10; A01H 1/02; C12N 15/10; C12N 15/31
(52) U.S. Cl. .................. 800/306; 800/266; 800/267; 800/268; 800/271; 800/274; 800/278; 800/288; 800/287; 800/300; 800/303; 435/91.2; 435/418; 435/419; 435/468
(58) Field of Search ................... 800/306, 303, 800/278, 260, 271, 274, 266, 267, 268, 300, 288, 287; 435/468, 419, 418, 91.2

(56) References Cited

U.S. PATENT DOCUMENTS 6,025,546 A * 2/2000 Michiels et al. ............ 800/303
6,333,449 B1 * 12/2001 Michiels et al. ............ 800/300

FOREIGN PATENT DOCUMENTS

| EP | 0 270 615 B1 | 6/1988 |
| EP | 0 116 718 B2 | 5/1996 |
| EP | 0 344 029 B1 | 1/1997 |
| WO | WO 96/26283 | 8/1996 |

OTHER PUBLICATIONS

Welsh et al. Nucleic Acids Research 18 (24): 7213–7218, Dec. 1990.*
Reynaerts et al. Scientia Horticulturae, vol. 55, No. 1–2, pp. 125–139, 1993 (Abstract only).*
Zhong et al. Acta Botanica Sinica, vol. 38, No. 38, No. 7, pp. 582–585, 1996 (Abstract only).*
"Induction of male sterility in plants by a chimaeric ribonuclease gene," Mariani et al., Nature, vol. 327, Oct. 25, 1990, pp. 737–741.
"Engineered fertility control in transgenic *Brassica napus* L.: Histochemical analysis of anther development," De Block et al., , Planta (1993), 189: pp. 218–225.
"Genetic transformation of *Brassica*," Poulsen, G.B., Plant Breeding 115, 1996, pp. 209–225.
"A combined used of microprojectile bombardment and DNA imbibition enhances transformation frequencey of canola (*Brassica napus* L.)," Chen et al., Theor Appl Genet (1994), pp. 187–192.
"Transformation of *Brassica napus* and *Brassica oleracea* Using Agrobacterium tumefaciens and the Expression of the bar and neo Genes in the Transgenic Plants," De Block et al., Plant Physiol. (1989), pp. 694–701.

* cited by examiner

Primary Examiner—David T. Fox
(74) Attorney, Agent, or Firm—Frommer Lawrence & Haug LLP

(57) ABSTRACT

This invention relates to transgenic Brassica plants, plant material and seeds, characterized by harboring a specific transformation event, particularly by the presence of a male-sterility gene, at a specific location in the Brassica genome. The invention also relates to the seed deposited a the ATCC which will grow into a male sterile, herbicide resistant plant. The invention further provides a process producing a transgenic cell of a Brassica plant and a method of identifying a transgenic plant, or cells or tissues thereof. A kit for identifying the transgenic plants comprising the elite event of the prsent invention is also described. The Brassica plants of the invention combine the male-sterility phenotype with optimal agronomic performance, genetic stability and adaptability to different genetic backgrounds.

17 Claims, 5 Drawing Sheets

SEQUENCE LISTING

<160> NUMBER OF SEQ ID NOS: 14

<210> SEQ ID NO 1
<211> LENGTH: 5865
<212> TYPE: DNA
<213> ORGANISM: Artificial Sequence
<220> FEATURE:
<223> OTHER INFORMATION: Description of Artificial Sequence: T-DNA of
      plasmid pCO113

<400> SEQUENCE: 1

```
aattacaacg gtatatatcc tgccagtact cggccgtcga actcggccgt cgagtacatg      60
gtcgataaga aaaggcaatt tgtagatgtt aattcccatc ttgaaagaaa tatagtttaa     120
atatttattg ataaaataac aagtcaggta ttatagtcca agcaaaaaca taaatttatt     180
gatgcaagtt taaattcaga aatatttcaa taactgatta tatcagctgg tacattgccg     240
tagatgaaag actgagtgcg atattatgtg taatacataa attgatgata tagctagctt     300
agctcatcgg gggatcctag aacgcgtgat ctcagatctc ggtgacgggc aggaccggac     360
ggggcggtac cggcaggctg aagtccagct gccagaaacc cacgtcatgc cagttcccgt     420
gcttgaagcc ggccgcccgc agcatgccgc gggggggcata tccgagcgcc tcgtgcatgc     480
gcacgctcgg gtcgttgggc agcccgatga cagcgaccac gctcttgaag ccctgtgcct     540
ccagggactt cagcaggtgg gtgtagagcg tggagcccag tcccgtccgc tggtggcggg     600
gggagacgta cacggtcgac tcggccgtcc agtcgtaggc gttgcgtgcc ttccagggggc     660 ccgcgtaggc gatgccggcg acctcgccgt ccacctcggc gacgagccag ggatagcgct     720
cccgcagacg gacgaggtcg tccgtccact cctgcggttc ctgcggctcg gtacggaagt     780
```

-continued

```
tgaccgtgct tgtctcgatg tagtggttga cgatggtgca gaccgccggc atgtccgcct      840
cggtggcacg gcggatgtcg gccgggcgtc gttctgggtc cattgttctt ctttactctt      900
tgtgtgactg aggtttggtc tagtgctttg gtcatctata taatgata acaacaatga       960 gaacaagctt tggagtgatc ggagggtcta ggatacatga gattcaagtg gactaggatc     1020
tacaccgttg gattttgagt gtggatatgt gtgaggttaa ttttacttgg taacggccac     1080
aaaggcctaa ggagaggtgt tgagacccct atcggcttga accgctggaa taatgccacg     1140
tggaagataa ttccatgaat cttatcgtta tctatgagtg aaattgtgtg atggtggagt     1200
ggtgcttgct cattttactt gcctggtgga cttggcccctt tccttatggg gaatttatat    1260
tttacttact atagagcttt cataccttt ttttaccttg gatttagtta atatataatg      1320
gtatgattca tgaataaaaa tgggaaattt ttgaatttgt actgctaaat gcataagatt     1380
aggtgaaact gtggaatata tattttttc atttaaaagc aaaatttgcc ttttactaga      1440
attataaata tagaaaaata tataacattc aaataaaaat gaaataaga actttcaaaa      1500 aacagaacta tgtttaatgt gtaaagatta gtcgcacatc aagtcatctg ttacaatatg     1560
ttacaacaag tcataagccc aacaaagtta gcacgtctaa ataaactaaa gagtccacga     1620
aaatattaca aatcataagc ccaacaaagt tattgatcaa aaaaaaaaa cgcccaacaa      1680 agctaaacaa agtccaaaaa aaacttctca agtctccatc ttcctttatg aacattgaaa     1740
actatacaca aaacaagtca gataaatctc tttctgggcc tgtcttccca acctcctaca    1800
tcacttccct atcggattga atgttttact tgtaccttt ccgttgcaat gatattgata     1860
gtatgtttgt gaaaactaat agggttaaca atcgaagtca tggaatatgg atttggtcca    1920
agattttccg agagctttct agtagaaagc ccatcaccag aaatttacta gtaaaataaa    1980
tcaccaatta ggtttcttat tatgtgccaa attcaatata attatagagg atatttcaaa    2040
tgaaaacgta tgaatgttat tagtaaatgg tcaggtaaga cattaaaaaa atcctacgtc    2100
agatattcaa cttaaaaaat tcgatcagtg tggaattgta caaaaatttg ggatctacta    2160
tatatatata atgctttaca acacttggat tttttttgg aggctggaat ttttaatcta    2220
catatttgtt ttggccatgc accaactcat tgtttagtgt aatactttga ttttgtcaaa    2280
tatatgtgtt cgtgtatatt tgtataagaa tttctttgac catatacaca cacacatata    2340
tatatatata tatatattat atatcatgca ctttaattg aaaaaataat atatatatat    2400
atagtgcatt ttttctaaca accatatatg ttgcgattga tctgcaaaaa tactgctaga    2460
gtaatgaaaa atataatcta ttgctgaaat tatctcagat gttaagattt tcttaaagta    2520
aattctttca aattttagct aaaagtcttg taataactaa agaataatac acaatctcga    2580
ccacggaaaa aaaacacata ataaatttga atttcgaccg cggtacccgg aattcgagct    2640
cggtacccgg ggatcttccc gatctagtaa catagatgac accgcgcgcg ataatttatc    2700
ctagtttgcg cgctatattt tgttttctat cgcgtattaa atgtataatt gcgggactct    2760
aatcataaaa acccatctca taaataacgt catgcattac atgttaatta ttacatgctt    2820
aacgtaattc aacagaaatt atatgataat catcgcaaga ccggcaacag gattcaatct    2880
taagaaactt tattgccaaa tgtttgaacg atctgcttcg gatcctctag agccggaaag    2940
tgaaattgac cgatcagagt ttgaagaaaa atttattaca cactttatgt aaagctgaaa    3000
aaaacggcct ccgcaggaag ccgttttttt cgttatctga tttttgtaaa ggtctgataa    3060
tggtccgttg ttttgtaaat cagccagtcg cttgagtaaa gaatccggtc tgaatttctg    3120
```

-continued

```
aagcctgatg tatagttaat atccgcttca cgccatgttc gtccgctttt gcccgggagt    3180
ttgccttccc tgtttgagaa gatgtctccg ccgatgcttt tccccggagc gacgtctgca    3240
aggttcccct tgatgccac ccagccgagg gcttgtgctt ctgattttgt aatgtaatta     3300
tcaggtagct tatgatatgt ctgaagataa tccgcaaccc cgtcaaacgt gttgataacc    3360
ggtaccatgg tagctaattt cttaagtaa aactttgat ttgagtgatg atgttgtact      3420
gttacacttg caccacaagg gcatatatag agcacaagac atacacaaca acttgcaaaa    3480
ctaacttttg ttggagcatt tcgaggaaaa tggggagtag caggctaatc tgagggtaac    3540
attaaggttt catgtattaa tttgttgcaa acatggactt agtgtgagga aaaagtacca    3600
aaattttgtc tcaccctgat ttcagttatg gaaattacat tatgaagctg tgctagagaa    3660
gatgtttatt ctagtccagc cacccacctt atgcaagtct gcttttagct tgattcaaaa    3720
actgatttaa tttacattgc taaatgtgca tacttcgagc ctatgtcgct ttaattcgag    3780
taggatgtat atattagtac ataaaaaatc atgtttgaat catctttcat aaagtgacaa    3840
gtcaattgtc ccttcttgtt tggcactata ttcaatctgt taatgcaaat tatccagtta    3900
tacttagcta gatatccaat tttgaataaa aatagctctt gattagtaaa ccggatagtg    3960
acaaagtcac atatccatca aacttctggt gctcgtggct aagttctgat cgacatgggg    4020
ttaaaattta aattgggaca cataaatagc ctatttgtgc aaatctcccc atcgaaaatg    4080
acagattgtt acatggaaaa caaaaagtcc tctgatagaa gtcgcaaagt atcacaattt    4140
tctatcgaga gatagattga aagaagtgca gggaagcggt taactggaac ataacacaat    4200
gtctaaatta attgcattcg ctaaccaaaa agtgtattac tctctccggt ccacaataag    4260
ttatttttg gccctttttt tatggtccaa aataagtgag ttttttagat ttcaaaaatg     4320
atttaattat ttttttacta cagtgcccct ggagtaaatg gtgttggagt atgtgttaga    4380
aatgtttatg tgaagaaata gtaaaggtta atatgatcaa tttcattgct atttaatgtt    4440
aaaatgtgaa tttcttaatc tgtgtgaaaa caaccaaaaa atcacttatt gtggaccgga    4500
gaaagtatat aaatatatat ttggaagcga ctaaaaataa acttttctca tattatacga    4560
acctaaaaac agcatatggt agtttctagg gaatctaaat cactaaaatt aataaaagaa    4620
gcaacaagta tcaatacata tgatttacac cgtcaaacac gaaattcgta aatatttaat    4680
ataataaaga attaatccaa atagcctccc accctataac ttaaactaaa aataaccagc    4740
gaatgtatat tatatgcata atttatatat taaatgtgta taatcatgta taatcaatgt    4800
ataatctatg tatatggtta gaaaaagtaa acaattaata tagccggcta tttgtgtaaa    4860
aatccctaat ataatcgcga cggatccccg ggaattccgg ggaagcttag atccatgcag    4920
atctgatcat gagcggagaa ttaagggagt cacgttatga cccccgccga tgacgcggga    4980
caagccgttt tacgtttgga actgacagaa ccgcaacgat tgaaggagcc actcagccgc    5040
gggtttctgg agtttaatga gctaagcaca tacgtcagaa accattattg cgcgttcaaa    5100
agtcgcctaa ggtcactatc agctagcaaa tatttcttgt caaaaatgct ccactgacgt    5160
tccataaatt cccctcggta tccaattaga gtctcatatt cactctcaat ccaaaccatg    5220
aaaaagcag tcattaacgg ggaacaaatc agaagtatca gcgacctcca ccagacattg    5280
aaaaaggagc ttgcccttcc ggaatactac ggtgaaaacc tggacgcttt atgggattgt    5340
ctgaccggat gggtggagta cccgctcgtt ttggaatgga gcagtttga acaaagcaag    5400
cagctgactg aaaatggcgc cgagagtgtg cttcaggttt ccgtgaagc gaaagcggaa     5460
ggctgcgaca tcaccatcat actttcttaa tacgatcaat gggagatgaa caatatggaa    5520
```

```
acacaaaccc gcaagcttgg tctagaggat cccccgatga gctaagctag ctatatcatc    5580
aatttatgta ttacacataa tatcgcactc agtctttcat ctacggcaat gtaccagctg    5640
atataatcag ttattgaaat atttctgaat ttaaacttgc atcaataaat ttatgttttt    5700
gcttggacta taatacctga cttgttattt tatcaataaa tatttaaact atatttcttt    5760
caagatggga attaacatct acaaattgcc ttttcttatc gaccatgtac atcgagctct    5820
ccccagatct gcatggagcc atttacaatt gaatatatcc tgccg                    5865
```

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer
      MDB355

<400> SEQUENCE: 2
gtaacataga tgacaccgcg c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer
      MDB008

<400> SEQUENCE: 3
atagggtggg aggctatttg g                                              21

<210> SEQ ID NO 4
<211> LENGTH: 15
<212> TYPE: DNA
<213> ORGANISM: Artificial Sequence
<220> FEATURE:
<221> NAME/KEY: variation
<222> LOCATION: (1)..(15)
<223> OTHER INFORMATION: N stands for any nucleic acid
<221> NAME/KEY: variation
<222> LOCATION: (1)..(15)
<223> OTHER INFORMATION: S stands for G or C
<221> NAME/KEY: variation
<222> LOCATION: (1)..(15)
<223> OTHER INFORMATION: W stands for A or T/U
<221> NAME/KEY: variation
<222> LOCATION: (1)..(15)
<223> OTHER INFORMATION: Description of Artificial Sequence: primer
      MDB285

<400> SEQUENCE: 4
ntcgastwts gwgtt                                                     15

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: primer
      MDB251

<400> SEQUENCE: 5 ggatccccccg atgagctaag ctagc                                         25

<210> SEQ ID NO 6
<211> LENGTH: 22
```

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer
      MDB193

<400> SEQUENCE: 6
tcatctacgg caatgtacca gc                                              22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer
      MDB258

<400> SEQUENCE: 7
ctacggcaat gtaccagctg                                                 20

<210> SEQ ID NO 8
<211> LENGTH: 415
<212> TYPE: DNA
<213> ORGANISM: Artificial Sequence
<220> FEATURE:
<223> OTHER INFORMATION: Description of Artificial Sequence: 5' border
      flanking region of elite event MS-B2
<221> NAME/KEY: misc_feature
<222> LOCATION: (1)..(234)
<223> OTHER INFORMATION: plant DNA
<221> NAME/KEY: misc_feature
<222> LOCATION: (235)..(415)
<223> OTHER INFORMATION: T-DNA

<400> SEQUENCE: 8
gtcgagtttg gtgttcatga ttttgggttt tgactcttca ccattacata ttgaaactct     60
tacggatgag aacaactcac aagcattaat catgttcata taaatatatg tacattatac    120
gtatatatac acgtatacaa atagtagcga agaaatccat gtaaagcagc aggggggcacc   180 atggtttcaa gtattatata attataatta taattatggt aggatgtaca tggccgataa    240
gaaaaggcaa tttgtagatg ttaattccca tcttgaaaga aatatagttt aaatatttat    300
tgataaaata acaagtcagg tattatagtc caagcaaaaa cataaattta ttgatgcaag    360
tttaaattca gaaatatttc aataactgat tatatcagct ggtacattgc cgtag         415

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: primer MDB8

<400> SEQUENCE: 9
tcagaagtat cagcgacctc cacc                                            24

<210> SEQ ID NO 10
<211> LENGTH: 416
<212> TYPE: DNA
<213> ORGANISM: Artificial Sequence
<220> FEATURE:
<223> OTHER INFORMATION: Description of Artificial Sequence: 3' border
      flanking region of elite event MS-B2
<221> NAME/KEY: misc_feature
<222> LOCATION: (1)..(193)
<223> OTHER INFORMATION: T-DNA
<221> NAME/KEY: misc_feature
<222> LOCATION: (194)..(416)

```
-continued

<223> OTHER INFORMATION: plant DNA

<400> SEQUENCE: 10
ctacggcaat gtaccagctg atataatcag ttattgaaat atttctgaat ttaaacttgc      60
atcaataaaw ttatgttttt gcttggacta taatacctga cttgttattt tatcaataaa    120
tatttaaact atatttcttt caagatggga attaacatct acaaattgcc ttttcttatc    180
gaccatgtac atcctaccat aattataatt ataattatat aatactgaaa ccatggtgcc    240
ccctgctgct ttacatggat ttctccgcta ctatttgtat acgtgtatat ataccgtata    300
atgtacatat atttatatga acatgattaa tgcttgtgag ttgttctcat ccgtaagagt    360
ttcaatatgt aatggtgaag agtcaaaacc caaaatcatg aacacccaaa ctcgat        416

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer
      MDB371

<400> SEQUENCE: 11
gaaatccatg taaagcagca ggg                                              23

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: MDB201

<400> SEQUENCE: 12
gcttggacta taatacttga c                                                21

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer CV27

<400> SEQUENCE: 13
aacgagtgtc agctagacca gc                                               22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer CVZ8

<400> SEQUENCE: 14
cgcagttctg tgaacatcga cc                                               22
```

MALE-STERILE BRASSICA PLANTS AND METHODS FOR PRODUCING SAME

FIELD OF THE INVENTION

This invention pertains to transgenic Brassica plants, plant material and seeds, characterized by harboring a specific transformation event, particularly by the presence of a male-sterility gene, at a specific location in the Brassica genome. The Brassica plants of the invention combine the male-sterility phenotype with optimal agronomic performance, genetic stability and adaptability to different genetic backgrounds.

All documents cited herein are hereby incorporated herein by reference.

BACKGROUND OF THE INVENTION

The phenotypic expression of a transgene in a plant is determined both by the structure of the gene itself and by its location in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps which include extensive genetic characterization, breeding, and evaluation in field trials.

The term "rapeseed" covers every seed of the Brassica species. Brassica is cultivated from China and India to Finland and Canada as one of the most valuable oil crops. Most Brassica types belong to the family of Cruciferae. They originated as a diploid species having aneuploid chromosome numbers ranging from 7 (*Brassica fruticulosa*) to 12 (*Sinapsis alba*). The most extensively grown Brassica species in Canada is known as turnip rape, or *Brassica campestris* (aa, n=10). *Brassica oleracea* (cc, n=9) has diversified in recent evolutionary history into at least six major horticultural types, including broccoli, cauliflower and cabbage. *Brassica nigra* (bb, n=8) or black mustard is a less important crop commercially and is mainly known for its seeds from which mustard was originally made. From these basic types, amphiploid hybrids have been derived in more recent evolutionary stages by intercrossing. The most important of these are *Brassica napus* (aacc), of which the winter types provide the highest rapeseed yields in northern Europe and *Brassica juncea* (aabb) or brown mustard which is one of the major oil crops of the Indian sub-continent. Though intercrossing between different Brassica species (particularly those with compatible genomes) is possible and often done for breeding purposes, not all traits (or genes) will be able to be transferred from one species to the other or, when transferred to a different species, will retain identical characteristics (or expression patterns). Thus, a genetic locus conferring optimal expression of a natural or chimeric gene in one Brassica species, will not necessarily have the same effect in another.

Brassica species are bisexual and typically 60–70% self pollinated. The production of hybrids and introduction of genetic variation as a basis for selection was traditionally dependent on the adaptation of natural occurring phenomena such as self-incompatibility and cytoplasmic male sterility. Artificial pollination control methods such as manual emasculation or the use of gametocides are not widely applied in Brassica breeding due to their limited practicability and high cost respectively.

Transgenic methods have been developed for the production of male or female-sterile plants, which provide interesting alternatives to the traditional techniques. EP 0,344,029 describes a system for obtaining nuclear male sterility whereby plants are transformed with a male-sterility gene, which comprises for example a DNA encoding a barnase molecule under the control of a tapetum specific promoter TA29, which when incorporated into a plant ensures selective destruction of taptetum cells. Transformation of tobacco and oilseed rape plants with such a gene resulted in plants in which pollen formation was completely prevented (Mariani et al. 1990, Nature 347: 737–741). Cytochemical and histochemical analysis of anther development of *Brassica napus* plants comprising the chimeric pTA29:barnase gene is described by De Block and De Brouwer (1993, Planta 189:218–225).

To restore fertility in the progeny of a male-sterile plant, a system was developed whereby the male-sterile plant is crossed with a transgenic plant carrying a fertility-restorer gene, which when expressed is capable of inhibiting or preventing the activity of the male-sterility gene (U.S. Pat. Nos. 5,689,041; 5,792,929; De Block and De Brouwer, supra). The use of coregulating genes in the production of male-sterile plants to increase the frequency of transformants having good agronomical performance is described in WO96/26283. Typically, when the sterility DNA encodes a barnase, the coregulating DNA will encode a barstar.

Successful genetic transformation of Brassica species has been obtained by a number of methods including Agrobacterium infection (as described, for example in EP 0,116,718 and EP 0,270,882), microprojectile bombardment (as described, for example by Chen et al., 1994, Theor. Appl. Genet. 88:187–192) and direct DNA uptake into protoplasts (as described, for example by De Block et al. 1989, Plant Physiol. 914:694–701; Poulsen, 1996, Plant Breeding 115:209–225).

However, the foregoing documents fail to teach or suggest the present invention.

SUMMARY OF THE INVENTION

The invention relates to a transgenic Brassica plant, the genomic DNA of which is characterized by one or both of the following characteristics:

a) the genomic DNA is capable of yielding at least two, preferably at least three, more preferably at least four, most preferably five of the restriction fragments or sets of restriction fragments selected from the group of:

i) One set of NcoI fragments, one with a length of between 5077 and 14057 bp, preferably of about 6000 bp, and one with a length of between 2450 and 2838 bp, preferably of about 2500 bp;

ii) one set of EcoRV fragments wherein one has a length of between 5077 and 14057 bp, preferably of about 5500 bp and one with a length of between 4507 and 5077 bp, preferably of about 4800 bp;

iii) one set of MunI fragments, one with a length of between 5077 and 14057 bp, preferably with a length of about 5700 bp, and one with a length of between 2838 and 4799 bp, preferably of about 4500 bp;

iv) one HindIII fragment, with a length of between 2838 and 4507 bp, preferably with a length of about 3938 bp, v) one EcoRI fragment, with a length of between 1989 and 2450 bp, preferably of about 2262 bp;

wherein each of the restriction fragments is capable of hybridizing under standard stringency conditions, with the +/−2000 bp fragment obtainable by PCR amplification of a fragment of SEQ ID No. 1, using the probes having SEQ ID No. 2 and SEQ ID No. 3 and/or b) the genomic DNA can be used to amplify a DNA fragment of between 160 and 200 bp, preferably of about 183 bp, using a polymerase chain reaction with two primers having the nucleotide sequence of SEQ ID No.11 and SEQ ID No.12 respectively.

The present invention further relates to a transgenic Brassica plant, or seed, cells or tissues thereof, the genomic DNA of which is characterized in that it is capable of yielding at least two, preferably at least three, for instance at least four, more preferably five of the sets of restriction fragments selected from the group described under a) above comprising the sets of restriction fragments described under a) i), ii), iii), iv), and v) above, whereby the selection can include any combination of i), ii), iii), iv), and v) described under a) above.

The present invention further relates to a transgenic Brassica plant, or seed, cells, tissues or progeny thereof, the genomic DNA of which is characterized by both the characteristics described under a) and b) above.

The present invention further relates to a transgenic male-sterile Brassica plant, the genomic DNA of which is characterized by one, preferably by both the characteristics described under a) and b) above.

The invention also relates to the seed deposited at the ATCC, under accession number PTA-850, which will grow into a male sterile, herbicide resistant plant. The seed of ATCC deposit number PTA-850 comprises about 50% seed comprising the elite event of the invention, which will grow into male sterile, PPT tolerant plants. The seed can be sown and the growing plants can be treated with PPT or Liberty™ as described herein, to obtain 100% male-sterile PPT tolerant plants comprising the elite event of the invention. The invention further relates to cells, tissues, progeny and descendants from a plant comprising the elite event of the invention grown from the seed deposited at the ATCC having accession number PTA-850. The invention further relates to plants obtainable by propagation of and/or breeding with a Brassica plant comprising the elite event of the invention grown from the seed deposited at the ATCC having accession number PTA-850.

The invention further relates to plants, seeds, cells or tissues comprising a foreign DNA sequence, preferably a male-sterility gene as described herein, integrated into the chromosomal DNA in a region which comprises the plant DNA sequence of SEQ ID No. 8 and/or SEQ ID No. 10, or a sequence which has at least 85% sequence identity to a sequence comprising the plant DNA sequence of SEQ ID No. 8 and/or SEQ ID No. 10.

The invention further provides a process for producing a transgenic cell of a Brassica plant, which comprises inserting a recombinant DNA molecule into a region of the chromosomal DNA of a Brassica cell which comprises the plant DNA sequence of SEQ ID No. 8 and/or SEQ ID No. 10, or a sequence which has at least 85% sequence identity with a sequence comprising the plant DNA sequence of SEQ ID No. 8 and/or SEQ ID No. 10, and, optionally, regenerating a Brassica plant from the transformed *Brassica cell.*

The invention further relates to a method for identifying a transgenic plant, or cells or tissues thereof, which method comprises establishing one or both of the following characteristics of the genomic DNA of the transgenic plant, or its cells or tissues:

a) the genomic DNA is capable of yielding at least two, preferably at least three, more preferably at least four, most preferably five of the restriction fragments or sets of restriction fragments selected from the group of:

i) One set of NcoI fragments, one with a length of between 5077 and 14057 bp, preferably of about 6000 bp, and one with a length of between 2450 and 2838 bp, preferably of about 2500 bp;

ii) one set of EcoRV fragments wherein one has a length of between 5077 and 14057 bp, preferably of about 5500 bp and one with a length of between 4507 and 5077 bp, preferably of about 4800 bp;

iii) one set of MunI fragments, one with a length of between 5077 and 14057 bp, preferably with a length of about 5700 bp, and one with a length of between 2838 and 4799 bp, preferably of about 4500 bp;

iv) one HindIII fragment, with a length of between 2838 and 4507 bp, preferably with a length of about 3938 bp, v) one EcoRI fragment, with a length of between 1989 and 2450 bp, preferably of about 2262 bp;

wherein each of the restriction fragments is capable of hybridizing under standard stringency conditions, with the +/−2000 bp fragment obtainable by PCR amplification of a fragment of SEQ ID No. 1, using the probes having SEQ ID No. 2 and SEQ ID No. 3 and/or b) the genomic DNA can be used to amplify a DNA fragment of between 160 and 200 bp, preferably of about 183 bp, using a polymerase chain reaction with two primers having the nucleotide sequence of SEQ ID No.11 and SEQ ID No.12 respectively.

The invention further relates to a kit for identifying the transgenic plants comprising the elite event of the present invention, which kit comprises at least two PCR probes, one of which recognizes a sequence within the T-DNA of the elite event, the other recognizing a sequence within the 5' or 3' border flanking region of the elite event of the invention, preferably the PCR primers having the nucleotide sequence of SEQ ID No. 11 and SEQ ID No. 12, respectively, for use in the PCR identification protocol.

BRIEF DESCRIPTION OF THE DRAWINGS

The following detailed description, given by way of example, but not intended to limit the invention to specific embodiments described, may be understood in conjunction with the accompanying Figures, incorporated herein by reference, in which.

DETAILED DESCRIPTION OF THE INVENTION

Figure 1:
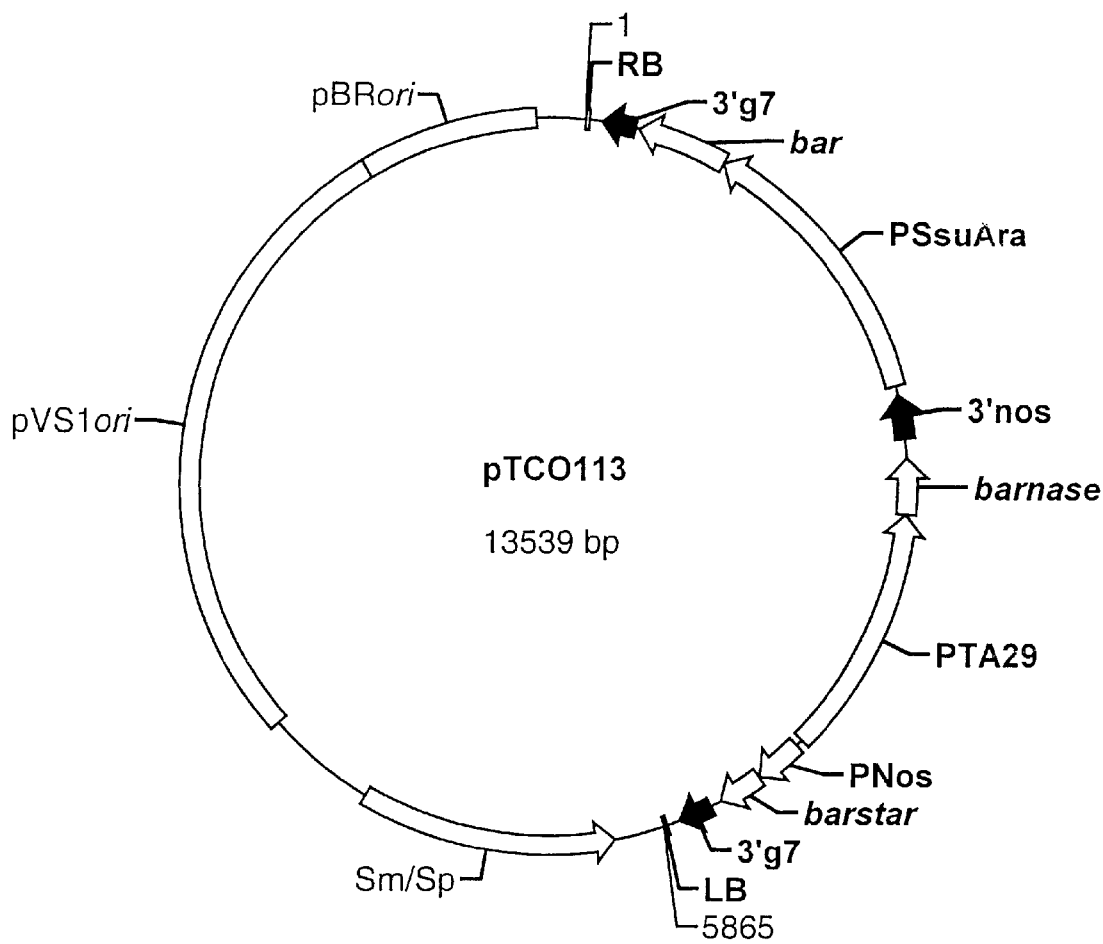
FIG. 1. Plasmid map of pTCO113. The elements of plasmid PTCO113 are described in Example 2, Table 1.

The term "gene" as used herein refers to any DNA sequence comprising several operably linked DNA fragments such as a promoter and a 5' untranslated region (the 5'UTR), which together form the promoter region, a coding region (which may or may not code for a protein), and an untranslated 3' region (3'UTR) comprising a polyadenylation site. Typically in plant cells, the 5'UTR, the coding region and the 3'UTR are transcribed into an RNA which, in the case of a protein encoding gene, is translated into the protein. A gene may include additional DNA fragments such as, for example, introns. As used herein, a genetic locus is the position of a given gene in the genome of a plant.

The term "chimeric" when referring to a gene or DNA sequence is used to refer to the fact that the gene or DNA sequence comprises at least two functionally relevant DNA fragments (such as promoter, 5'UTR, coding region, 3'UTR, intron) that are not naturally associated with each other and originate, for example, from different sources. "Foreign" referring to a gene or DNA sequence with respect to a plant species is used to indicate that the gene or DNA sequence is not naturally found in that plant species, or is not naturally found in that genetic locus in that plant species. The term "foreign DNA" will be used herein to refer to a DNA sequence as it has incorporated into the genome of a plant as a result of transformation. The "transforming DNA" as used herein refers to a recombinant DNA molecule used for transformation. The transforming DNA usually comprises at least one "gene of interest" (e.g. a chimeric gene) which is capable of conferring one or more specific characteristics to the transformed plant. The term "recombinant DNA molecule" is used to exemplify and thus can include an isolated nucleic acid molecule which can be DNA and which can be obtained through recombinant or other procedures.

As used herein the term "transgene" refers to a gene of interest as incorporated in the genome of a plant. A "transgenic plant" refers to a plant comprising at least one transgene in the genome of all of its cells.

The foreign DNA present in the plants of the present invention will preferably comprise two genes of interest, more specifically, a male-sterility gene and a coregulating gene.

A male-sterility gene as used herein refers to a gene which upon expression in a plant renders the plant incapable of producing fertile pollen. An example of a male sterility gene is a gene comprising a DNA sequence encoding barnase, under the control of a promoter directing expression in tapetum cells. More specifically, according to the present invention, a preferred embodiment of the male-sterility gene comprises a DNA encoding barnase under control of the promoter of the TA29 gene of Nicotiana tabacum, also referred to as "TA29-barnase" herein. The TA29 promoter has a "tapetum selective" expression pattern in Brassica (De Block and Debrouwer, Planta 189:218–225, 1993).

A coregulating gene as used herein refers to a gene, which when introduced into plant cells together with another chimeric gene, increases the frequency of transformants having good agronomical performance. An example of a coregulating gene for use together with a male-sterility gene encoding barnase, is a gene comprising a DNA sequence encoding barstar, under the control of a promoter capable of directing expression in non-stamen cells or which directs weak expression in stamen cells. More specifically, in the elite event of the present invention the coregulating gene comprises a DNA encoding barstar under control of the nopaline synthase gene from the T-DNA of Agrobacterium tumefaciens (Depicker et al., 1984, J. Mol. Appl. Genet. 1:3403), also referred to as "PNOS-barstar" herein.

A fertility restorer gene as used herein refers to a gene which upon expression in a plant comprising a male-sterility gene, is capable of preventing expression of the male-sterility gene, restoring fertility in the plant.

The incorporation of a recombinant DNA molecule in the plant genome typically results from transformation of a cell or tissue (or from another genetic manipulation). The particular site of incorporation is either due to chance or is at a predetermined location (if a process of targeted integration is used).

The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the recombinant DNA into the plant genome can be associated with a deletion of plant DNA, referred to as "target site deletion". A "flanking region" or "flanking sequence" as used herein refers to a sequence of at least 20 bp, preferably at least 50 bp, and up to 5000 bp of the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the recombinant DNA is introduced into a plant through traditional crossing, its insertion site in the plant genome, or its flanking regions will generally not be changed. An "insertion region" as used herein refers to the region corresponding to the region of at least 40 bp, preferably at least 100 bp, and up to more than 10000 bp, encompassed by the sequence which comprises the upstream and/or the downstream flanking region of a foreign DNA in the (untransformed) plant genome (and possibly including the insertion site and possible target site deletion). Taking into consideration minor differences due to mutations within a species, an insertion region will retain at least 85%, preferably 90%, more preferably 95%, and most preferably 100% sequence identity with the sequence comprising the upstream and downstream flanking regions of the foreign DNA in a given plant of that species.

Expression of a gene of interest refers to the fact that the gene confers on the plant one or more phenotypic traits (e.g. herbicide tolerance) that were intended to be conferred by the introduction of the recombinant DNA molecule—the transforming DNA—used during transformation (on the basis of the structure and function of part or all of the gene(s) of interest).

An event is defined as a (artificial) genetic locus that, as a result of genetic manipulation, carries a foreign DNA comprising at least one copy of the gene(s) of interest. The typical allelic states of an event are the presence or absence of the foreign DNA. As used herein an "MS" event will refer to an event carrying a transgene comprising "TA29-barnase" and "PNOS-barstar". An event is characterized phenotypically by the expression of the transgenes. At the genetic level, an event is part of the genetic makeup of a plant. At the molecular level, an event is characterized by the restriction map (e.g. as determined by Southern blotting) and/or by the upstream and/or downstream flanking sequences of the foreign DNA, and/or the molecular configuration of the foreign DNA comprising the transgenes. Usually transformation of a plant with a transforming DNA leads to a multitude of events, each of which is unique.

An elite event, as used herein, is an event which is selected from a group of events, obtained by transformation with the same transforming DNA or by back-crossing with plants obtained by such transformation, based on the expression and stability of the transgenes and its compatibility with optimal agronomic characteristics of the plant comprising it. Thus the criteria for elite event selection are one or more, preferably two or more, advantageously all of the following:

a) That the presence of the foreign DNA does not compromise other desired characteristics of the plant, such as those relating to agronomic performance or commercial value;

b) That the event is characterized by a well defined molecular configuration which is stably inherited and for which appropriate diagnostic tools for identity control can be developed;

c) That the gene(s) of interest show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use;

It is preferred that the foreign DNA is associated with a position in the plant genome that allows introgression into desired commercial genetic backgrounds.

The status of an event as an elite event is confirmed by introgression of the elite event in different relevant genetic backgrounds and observing compliance with one, two or all of the criteria e.g. a), b) and c) above.

Additionally, for the transforming DNA comprising a male sterility gene and a coregulating gene described herein, selection of the elite event will also be determined on the compatibility between this event and selected plants comprising a fertility restorer gene. More specifically, it will be ensured that the progeny, resulting from a cross between a plant carrying the male-sterility event as described herein and a plant homozygous for a fertility restorer gene, that this progeny in which at least the fertility restorer event is present, has the following characteristics:

a) adequate phenotypic expression of the fertility restored phenotype, i.e. male fertility; and b) phenotypic expression occurs at a commercially acceptable level in a range of environmental conditions in which plants carrying the two events are likely to be exposed in normal agronomic use;

An "elite event" thus refers to a genetic locus comprising a foreign DNA, which answers to the above-described criteria. A plant, plant material or progeny such as seeds can comprise one or more elite events in its genome.

The "diagnostic tools" developed to identify an elite event or the plant or plant material comprising an elite event, are based on the specific genomic characteristics of the elite event, such as, a specific restriction map of the genomic region comprising the foreign DNA and/or the sequence of the flanking region(s) of the foreign DNA. A "restriction map" as used herein refers to a set of Southern blot patterns obtained after cleaving plant genomic DNA with a particular restriction enzyme, or set of restriction enzymes and hybridization with a probe sharing sequence similarity with the foreign DNA under standard stringency conditions. Standard stringency conditions as used herein refers to the conditions for hybridization described herein or to the conventional hybridizing conditions as described by Sambrook et al. (1989) (Molecular Cloning: A Laboratory Manual, Second Edition, Cold Spring Harbour Laboratory Press, NY) which for instance can comprise the following steps: 1) immobilizing plant genomic DNA fragments on a filter, 2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, 3) adding the hybridization probe which has been labeled, 4) incubating for 16 to 24 hours, 5) washing the filter for 20 min. at room temperature in 1×SSC, 0.1% SDS, 6) washing the filter three times for 20 min. each at 68° C. in 0.2×SSC, 0.1% SDS, and 7) exposing the filter for 24 to 48 hours to X-ray film at −70° C. with an intensifying screen.

Due to the (endogenous) restriction sites present in a plant genome prior to incorporation of the foreign DNA, insertion of a foreign DNA will alter the specific restriction map of that genome. Thus, a particular transformant or progeny derived thereof can be identified by one or more specific restriction patterns. The conditions for determining the restriction map of an event are laid out in a "restriction map identification protocol". Alternatively, plants or plant material comprising an elite event can be identified by testing according to a PCR identification protocol. This is a PCR using primers which specifically recognize the elite event. Essentially, a set of primers is developed which recognizes a) a sequence within the 3' or 5' flanking sequence of the elite event and b) a sequence within the foreign DNA, which primers amplify a fragment (integration fragment) preferably of between 100 and 350 nucleotides. Preferably, a control is included of a set of primers which amplifies a fragment within a housekeeping gene of the plant species (preferably a fragment which is larger than the amplified integration fragment). The optimal conditions for the PCR, including the sequence of the specific primers is specified in a PCR identification protocol.

The present invention relates to the development of an elite event in Brassica, MS-B2, to the plants comprising this event, the progeny obtained from these plants and to the plant cells, or plant material derived from this event. Plants comprising elite event MS-B2 were obtained through transformation with pTCO 113 as described in example 1.

The recombinant DNAs used for the generation of the plants leading to the selection of elite event MS-B2 additionally comprises a DNA sequence encoding the enzyme phosphinothricin acetyl transferase and the 35S promoter of Cauliflower Mosaic Virus, wherein the sequence encoding phosphinothricin acetyl transferase is under the control of the 35S promoter (termed "35S-bar"). The 35S promoter has a "constitutive" expression pattern in Brassica, which means that it is significantly expressed in most cell types, during most of the plant life cycle. The expression of the 35S-bar gene in OSR plants confers resistance to herbicidal compounds phosphinothricin or bialaphos or glufosinate, or more generally, glutamine synthetase inhibitors, or salts or optical isomers thereof.

Brassica plants or plant material comprising MS-B2 can be identified according to the restriction map identification protocol described for MS-B2 in Example 5.1 herein. Briefly, Brassica genomic DNA is digested with a selection (preferably two to five) of the following restriction enzymes: NcoI, EcoRV, MunI, HindIII, EcoRI, is then transferred to nylon membranes and hybridized with the +/−2000 bp fragment obtained by PCR amplification of SEQ ID No. 1 with primers having SEQ ID No. 2 and SEQ ID No. 3 generated from plasmid pTCO113. It is then determined for each restriction enzyme used whether the following fragments can be identified:

NcoI: one fragment of between 5077 and 14057 bp, preferably of about 6000 bp, and one fragment of between 2450 and 2838 bp, preferably of about 2500 bp;

EcoRV: one fragment of between 5077 and 14057 bp, preferably of about 5,5 kbp and one fragment of between 4507 and 5077 bp, preferably of about 4800 bp;

MunI: one fragment of between 5077 and 14057 bp, preferably of about 5700 bp, one fragment of between 2838 and 4799 bp, preferably of about 4500 bp;

HindIII: one fragment of between 2838 and 4507 bp, preferably of about 3938 bp;

EcoRI: one fragment of between 1989 and 2450 bp, preferably of about 2262 bp;

The lengths of the DNA fragments are determined by comparison with a set of DNA fragments of known length, particularly the PstI fragments of phage lambda DNA. If the plant material after digestion with at least two, preferably at least three, particularly with at least 4, more particularly with all of these restriction enzymes, yields DNA fragments with the same length as those described above, the Brassica plant is determined to harbor elite event MS-B2.

Brassica plants or plant material comprising MS-B2 can also be identified according to the PCR identification protocol described for MS-B2 in Example 5.2 herein. Briefly, Brassica genomic DNA is amplified by PCR using a primer which specifically recognizes a flanking sequence of MS-B2, particularly the primer with the sequence of SEQ ID No 11, and a primer which recognizes a sequence in the foreign DNA, particularly the primer with the sequence of SEQ ID No.12. Endogenous Brassica DNA primers are used as controls. If the plant material yields a fragment of between 160 and 200 bp, preferably of about 183 bp, the Brassica plant is determined to harbor elite event MS-B2.

Plants harboring MS-B2 are phenotypically characterized by the fact that, in the absence of a restorer gene in their genome, they are male-sterile. A male sterile plant is defined as not being able to produce fertile pollen.

Plants harboring MS-B2 are also characterized by their glufosinate tolerance, which in the context of the present invention includes that plants are tolerant to the herbicide Liberty™. Tolerance to Liberty™ is defined by the criterium that spraying of the plants in the three to four leaf stage (3V to 4V) with at least 200 grams active ingredient/hectare (g.a.i./ha), preferably 400 g.a.i./ha, and possibly up to 1600 g.a.i./ha, does not kill the plants. Plants harboring MS-B2 can further be characterized by the presence in their cells of phosphinothricin acetyl transferase as determined by a PAT assay (De Block et al, 1987, supra).

Brassica plants as used herein refers to plants of the family of the Brassicacea, preferably plants comprising an A genome. Preferably the Brassica plant will belong to one of the species Brassica napus, Brassica rapa (or campestris), or Brassica juncea. Alternatively, the plant can belong to a species originating from intercrossing of these Brassica species, such as B. napocampestris, or of an artificial crossing of one of these Brassica species with another species of the Cruciferacea.

Plants harboring MS-B2 can, for example, be obtained from seeds deposited at the ATCC under accession number PTA-850. Such plants can be further propagated to introduce the elite event of the invention into other cultivars of the same plant species. Seeds obtained from these plants contain the elite event stably incorporated into their genome.

The Brassica plants of this invention can be cultivated in a conventional way. The presence of the 35S-bar gene ensures that they are tolerant to glufosinate. Therefore, weeds in the fields where such Brassica plants are grown can be controlled by application of herbicides comprising glufosinate as an active ingredient (such as Liberty™).

Plants harboring MS-B2 are also characterized by having agronomical characteristics which are comparable to commercially available varieties of Brassica in the U.S. The agronomical characteristics of relevance are: plant height, strength/stiffness of straw, tendency to lodge, shatter resistance, drought tolerance, disease resistance (such as, but not limited to, Black leg, Light leafspot, Sclerotinia) and grain production and yield. It has been observed that the presence of a foreign DNA in the insertion region of the Brassica plant genome described herein, confers particularly interesting phenotypic and molecular characteristics to the plants comprising this event. More specifically, the presence of the Foreign DNA in this particular region in the genome of these plants results in stable phenotypic expression of the genes of interest without significantly compromising any aspect of desired agronomic performance of the plants, making them particularly suited for the production of hybrid seed. Thus, the insertion region, corresponding to a sequence comprising the plant DNA of SEQ ID No. 8 and/or SEQ ID No. 10, more particularly the insertion site of MS-B2 therein, is shown to be particularly suited for the introduction of a gene(s) of interest. More particularly, the insertion region of MS-B2 (corresponding to a DNA sequence of at least 40 bp in the genome of Brassica plants which corresponds to the plant DNA of SEQ ID No. 8 and/or SEQ ID No. 10, or a sequence of at least 40 bp which has at least 85% sequence similarity with the plant DNA of SEQ ID No. 8 and/or SEQ ID No. 10), is particularly suited for the introduction of plasmids comprising a male-sterility gene ensuring optimal expression of each of these genes in a plant without compromising agronomic performance.

A recombinant DNA molecule can be specifically inserted in an insertion region by targeted insertion methods. Such methods are well known to those skilled in the art and comprise, for example, homologous recombination using a recombinase such as, but not limited to the FLP recombinase from Saccharomyces cerevisiae (U.S. Pat. No. 5,527,695), the CRE recombinase from Escherichia coli phage P1 (published PCT application WO 9109957), the recombinase from pSRI of Saccharomyces rouxii (Araki et al. 1985, J Mol Biol 182:191–203), or the lambda phage recombination system (such as described in U.S. Pat. No. 4,673,640).

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Intelligenetics™ Suite (Intelligenetics Inc., CA). Sequences are indicated as "essentially similar" when such sequence have a sequence identity of at least about 75%, particularly at least about 80%, more particularly at least about 85%, quite particularly about 90%, especially about 95%, more especially about 100%, quite especially are identical. It is clear than when RNA sequences are said to be essentially similar or have a certain degree of sequence identity with DNA sequences, thymine (T) in the DNA sequence is considered equal to uracil (U) in the RNA sequence.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The following examples describe the development and characteristics of Brassica plants harboring the elite events MS-B2.

Unless otherwise stated, all recombinant DNA techniques are carried out according to standard protocols as described in Sambrook et al. (1989) *Molecular Cloning. A Laboratory Manual,* Second Edition, Cold Spring Harbour Laboratory Press, NY and in Volumes 1 and 2 of Ausubel et al. (1994) *Current Protocols in Molecular Biology,* Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

In the description and examples, reference is made to the following sequences:

SEQ ID No 1: T-DNA of plasmid pTCO113
SEQ ID No 2: primer MDB355
SEQ ID No 3: primer MLD008
SEQ ID No 4: primer MDB285
SEQ ID No 5: primer MDB251
SEQ ID No 6: primer MDB193
SEQ ID No 7: primer MDB258
SEQ ID No 8: Right (5') border flanking region of elite event MS-B2
SEQ ID No 9: primer MDB8
SEQ ID No 10: Left (3') border flanking region of elite event MS-B2
SEQ ID No 11: primer MDB371
SEQ ID No 12: primer MDB201
SEQ ID No 13: primer CVZ7 (BO1)
SEQ ID No 14: primer CVZ8 (B02)

EXAMPLES

Example 1

Transformation of Brassica with a Male-sterility Gene 1.1. Construction of the Chimeric DNA Comprising the Barnase Gene Under the Control of a Tapetum Specific Promoter (pTCO113).

Plasmid pTCO113 (SEQ ID No. 1) was essentially derived from the intermediate vector pGSV1. pGSV1 is itself derived from pGSC1700 (Cornelissen and Vandewielle, 1989), but comprises an artificial T-region consisting of the left and right border sequences of the TL-DNA form pTiB6S3 and multilinker cloning sites allowing the insertion of chimeric genes between the T-DNA border repeats. The pGSV1 vector is provided with a barstar gene on the plasmid mainframe, with regulatory signals for expression in *E. coli.* A full description of the DNA comprised between the border repeats of pTCO113 is given in Table 1:

TABLE 1

Nucleotide positions of the DNA comprised between the T-DNA border repeats of pTCO113

| Nt positions | Orientation | Description and references |
|---|---|---|
| 1–25 | | Right border repeat from the TL-DNA from pTiB6S3 (Gielen et al . . . (1984) The EMBO Journal 3: 835–846). |
| 26–53 | | Synthetic polylinker derived sequences |
| 54–90 | | Residual sequence from the TL-DNA at the right border repeat |
| 91–97 | | Synthetic polylinker derived sequences |
| 309–98 | Counter clockwise | The 3'untranslated end from the TL-DNA gene 7 (3'g7) of pTiB6S3 (Velten and Schell. (1985) Nucleic Acids Research 13: 6981–6998; Dhaese et al . . . (1983) The EMBO Journal 3: 835–846). |
| 310–331 | | Synthetic polylinker derived sequences |
| 883–332 | Counter clockwise | The coding sequence of the bialaphos resistance gene (bar) of *Streptomyces hygroscopicus* (Thompson et al . . . (1987) The EMBO Journal 6: 2519–2523). The N-terminal two codons of the wild type bar coding region have been substituted for the codons ATG and GAC respectively. |
| 2609–884 | Counter clockwise | The promoter from the atS1A ribulose-1,5-biphosphatecarboxylase small subunit gene from *Arabidopsis thaliana* (PssuAra) (Krebbers et al . . . (1988) Plant Molecular Biology 11: 745–759). |
| 2610–2659 | | Synthetic polylinker derived sequences |
| 2920–2660 | Counter clockwise | A 260 bp TaqI fragment from the 3'untranslated end of the nopaline synthase gene (3'nos) from the T-DNA of pTiT37 and containing plant polyadenylation signals (Depicker et al . . . (1982) Journal of Molecular and Applied Genetics 1: 561–573). |
| 2921–2936 | | Synthetic polylinker derived sequences |
| 3032–2937 | | 3'untranslated region downstream from the barnase coding sequence of *B. amyloliquefaciens* |
| 3368–3033 | Counter clockwise | The coding region of the barnase gene from *Bacillus amyloliquefaciens* (Hartley (1988) Journal of Molecular Biology 202: 913–915). |
| 4878–3369 | Counter clockwise | The promoter region of the anther-specific gene TA29 from *Nicotiana tabacum.* The promoter comprises the 1.5 kb of the sequence upstream from the ATG initiation codon (Seurinck et al . . . (1990) Nucleic Acids Research 18: 3403). |
| 4879–4924 | | Synthetic polylinker derived sequences |
| 4925–5215 | Clockwise | The promoter of the nopaline synthase gene from the T-DNA of pTiT37 of *Agrobacterium tumefaciens* (PNos). The nucleotide sequence of the PNos promoter is described by Depicker et al . . . (1982) Journal of Molecular and Applied Genetics 1: 561–573. |
| 5216–5217 | | Synthetic polylinker derived sequences |
| 5218–5490 | Clockwise | The coding region of the barstar gene of *Bacillus amyloliquefaciens* (Hartley (1988) Journal of Molecular Biology 202: 913–915). |
| 5491–5530 | | Sequence from the 3'untranslated end of the barstar gene from *Bacillus amyloliquefaciens* |

TABLE 1-continued

Nucleotide positions of the DNA comprised between
the T-DNA border repeats of pTCO113

| Nt positions | Orientation | Description and references |
|---|---|---|
| 5531–5554 | | Synthetic polylinker derived sequences |
| 5555–5766 | Clockwise | The 3'untranslated end from the TL-DNA gene 7 (3'g7) of pTiB6S3 (Velten and Schell. (1985) Nucleic Acids Research 13: 6981–6998; Dhaese et al . . . (1983) The EMBO Journal 3: 835–846). |
| 5767–5773 | | Synthetic polylinker derived sequence |
| 5774–5810 | | Residual sequences from the TL-DNA at the right border repeat |
| 5811–5840 | | Synthetic polylinker derived sequence |
| 5841–5865 | | Left border repeat from the TL-DNA from pTiB6S3 (Gielen et al . . . (1984) The EMBO Journal 3: 835–846). |

1.2. Transformation of *Brassica napus*

For transformation of *Brassica napus* the vector system as described by Deblaere et al. (1985, 1987) was used. The vector system consists of an Agrobacterium strain and two plasmid components: 1) a non-oncogenic Ti-plasmid (pGV400) and 2) an intermediate cloning vector based on plasmid pGSV1. The non-oncogenic Ti-plasmid from which the T-region has been deleted carries the vir genes required for transfer of an artificial T-DNA cloned on the second plasmid to the plant genome. The Agrobacterium strains resulting from the triparental mating between these components can be used for plant transformation.

Selection was done on phosphinothricin (PPT) at all stages except plantlet regeneration, which was done in the absence of PPT to accelerate growth. This resulted in a set of primary transformants (plants of generation $T_0$).

Example 2

Figure 2:
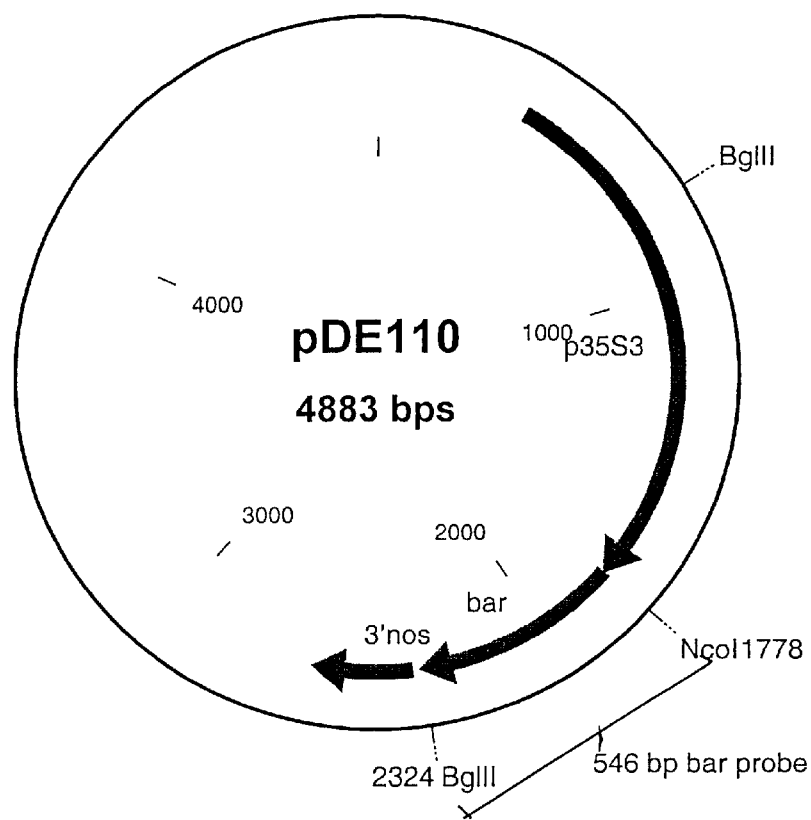
FIG. 2. Plasmid map of pDE110. The plasmid pDE110 comprises the coding sequence of the bialaphos resistance gene (bar) of *Streptomyces hygroscopicus,* (Thompson et al. 1987, The EMBO Journal 6:2519–2523), under control of the promoter of the 35S gene from Cauliflower Mosaic Virus (Odell et al., 1985, Nature 313:810–812). The BglIII-NcoI restriction fragment provides the bar probe.

Development of Events 2.1. Characterization of Transgenic Events 2.1.1. Southern Blot Analysis Presence of the foreign DNA and the number of gene insertions were checked by standard Southern blot analysis. Total genomic DNA is isolated from 1 g of shoot tissue according to Dellaporta (1983, Plant Molecular Biology Reporter, 1, vol.3, p.19–21 or Doyle et al. 1987, Phytochem. Bull. 19:11) and digested with EcoRV restriction enzyme. EcoRV has specific restriction sites within the T-DNA fragment, situated between the barnase and bar constructs. Southern analysis was performed with the following two probes:

"bar" probe: a 546 bp NcoI/BgIII fragment prepared from the vector pDE110 (FIG. 2).

Figure 3:
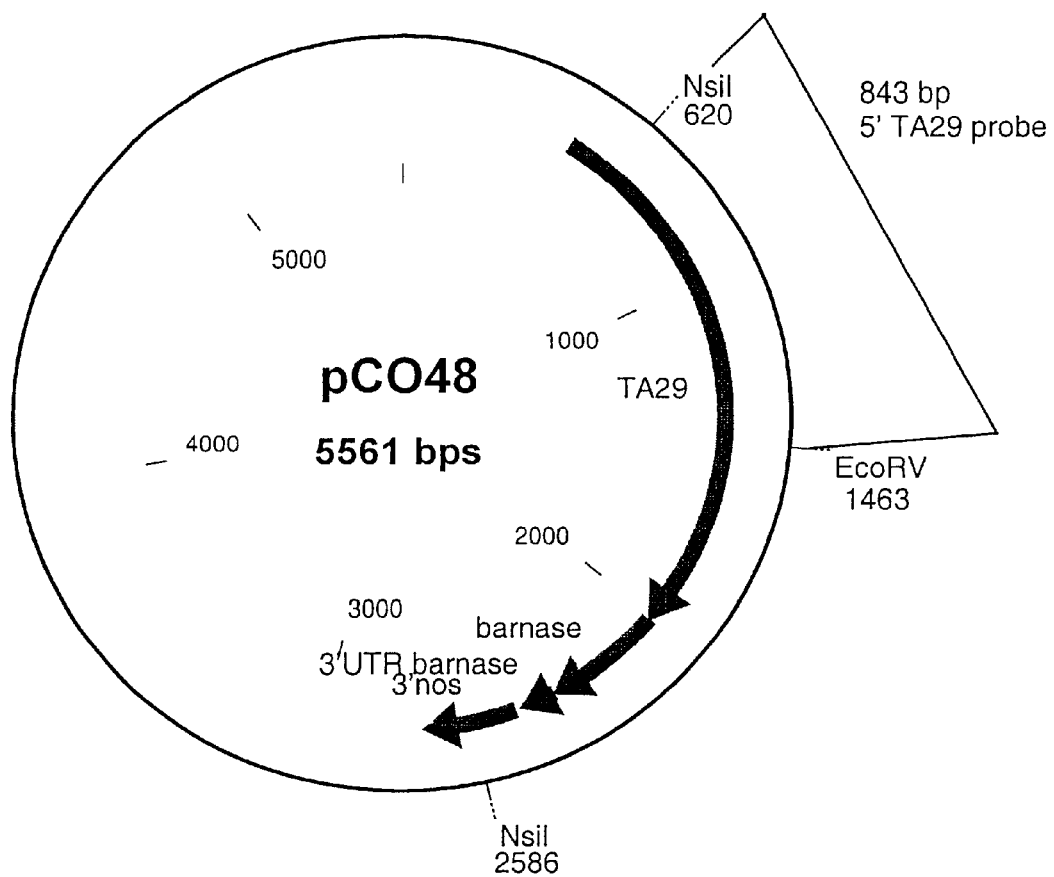
FIG. 3. Plasmid map of pCO48. The plasmid pCO48 comprises the coding sequence of the barnase gene from *Bacillus amyloliquefaciens* (Hartley, 1988, Journal of Molecular Biology 202: 913–915), under control of the promoter region of the anther specific gene TA29 from *Nicotiana tabacum* (Seurinck et al., 1990, Nucleic Acid Research 18: 3403). The EcoRV-NsiI restriction fragment provides the TA29 probe.

"PTA29" probe: a 843 bp NsiI/EcoRV fragment prepared from the vector pCO48 (FIG. 3).

Hybridization of the MS events with the bar probe yielded a 5 Kb band, while hybridization with the TA29 probe yielded a 4.6 Kb fragment. The relative band intensity provided an indication on whether plants were homozygous or hemizygous for the transgenic locus. Several events were found to have simple insertions. This was confirmed by the fact that the segregation pattern of the genes of interest could be explained by Mendelian inheritance of a simple locus.

2.1.2. General Plant Phenotype and Agronomic Performance $T_1$ plants of MS events were evaluated for a number of phenotypic traits including plant height, strength/stiffness of straw, tendency to lodge, winter-hardiness, shatter resistance, drought tolerance, disease resistance (Black leg, Light leafspot, Sclerotinia) and grain production and yield. Lines were evaluated to be similar (or improved) in displayed agronomic characteristics compared to the untransformed variety as well as a number of *Brassica napus* cultivars. In some cases, the plants segregated for somaclonal variation for one or more of the above-mentioned traits. Unless this resulted in the introduction of a commercially interesting phenotypic trait, these plants were discarded.

2.2. Development of Lines Carrying the MS Trait

The various $T_0$ hemizygous plantlets ("Ms/-") were transitioned from tissue culture, transferred to greenhouse soil. Presence of the foreign DNA and copy number was checked by southern blot analysis (described above). The plants were allowed to flower and sterility of flowers was evaluated. The $T_0$ plants were crossed with wildtype plants (-/-) to produce T1 seed (Ms-T1). T1 seeds were planted and grown up in the greenhouse. Plants were evaluated for tolerance to glufosinate ammonium. Ms-T1 plants were also evaluated for sterility/fertility segregation (in non-sprayed plants).

Ms-T1 plants comprising the foreign DNA were crossed with a tester plant homozygous for a fertility restorer gene (Rf/Rf), for the production of MsRf-F1 seed. This seed (Ms/-, Rf/- and -/-, Rf/-) was planted in the greenhouse and sprayed with Liberty™. Remaining F1 progeny is evaluated for fertility/sterility segregation to test whether the male sterility trait could be adequately restored in *Brassica napus* (fertility should be 100%).

The best events were selected for further testing. Ms-$T_1$, plants were crossed with a homozygous fertility restorer and the seed was planted in the field. Plants were evaluated for tolerance to the Liberty™ herbicide (at 800 grams active ingredient per hectare (g.a.i./ha) recommended dosage for farmers is 400 g.a.i./ha), for fertility/sterility segregation and for general phenotypic characteristics. The lines in which fertility was 100% restored and for which no negative penalties on phenotype or agronomic performance (detailed under 2.1.2.) was observed as compared to the wild-type isogenic control were selected.

2.3. Testing of MS Events in Different Genetic Backgrounds and in Different Locations The selected events are introduced into two different genetic backgrounds which are heterotically distinct, to prove that the MS event functions well and has no negative penalty on yield or quality in any background tested.

At the same time the selected MS event is tested in four to five different environments to ensure that there is no negative interaction between environment and the MS event.

2.4. Selection of a Candidate Elite Event

The above described selection procedure in the development of transgenic MS lines, yielded one elite event which displayed optimal expression of the genes comprised in the transforming DNA, i.e. resistance to glufosinate ammonium, a male-sterile phenotype and susceptibility to complete fertility restoration with a homozygous restorer line. This candidate elite event was named MS-B2.

Example 3

Characterization of Elite Event MS-B2

Once the MS-B2 event was identified as a candidate elite events in which expression of the genes of interest as well as overall agronomic performance were optimal, the locus of the foreign DNA was analyzed in detail on a molecular level. This included detailed Southern blot analysis (using multiple restriction enzymes) and sequencing of the flanking regions of the foreign DNA.

3.1. Southern Blot Analysis Using Multiple Restriction Enzymes

Leaf tissue was harvested from transgenic plants comprising event MS-B2 and control plants. Total genomic DNA was isolated from leaf tissue according to Dellaporta et al. (1983, Plant Molecular Biology Reporter, 1, vol.3, p.19–21). The DNA concentration of each preparation was determined by measuring the optical density in a spectrophotometer at a wavelength of 260 nm.

10 μg of genomic DNA was digested with restriction enzyme in a final reaction volume of 40 μl, applying conditions proposed by the manufacturer. The time of digestion and/or amount of restriction enzyme were adjusted to ensure complete digestion of the genomic DNA samples without non-specific degradation. After digestion, 4 μl of loading dye was added to the digested DNA samples, and they were loaded on a 1% agarose gel.

The following control DNAs were also loaded on the gel:
- a negative control with genomic DNA prepared from a non-transgenic Brassica plant.
  This negative control is used to confirm the absence of background hybridization.
- a DNA positive control: The amount representing one plasmid copy per genome is added to 1 μg of digested non-transgenic *Brassica napus* DNA. This reconstitution sample is used to show that the hybridizations are performed under conditions allowing hybridization of the probe with target sequences.

Phage Lambda DNA (strain CInd 1 ts 857 Sam 7, Life Technologies) digested with PstI was included as size standard.

After electrophoresis, the DNA samples (digested Brassica genomic DNA, controls and size standard DNA) were transferred to a Nylon membrane by capillary blotting during 12 to 16 hours.

As a probe, a DNA fragment was used which was obtained by PCR amplification of a fragment of pTCO113 with the following two primers:

| Probe | 5' 3' | position in pTCO113 |
|---|---|---|
| MDB355 | gTA.ACA.TAg.ATg.ACA.CCg.CgC (SEQ ID No. 2) | 2667–2687 |
| MLD008 | ATA.ggg.Tgg.gAg.gCT.ATT.Tgg (SEQ ID No. 3) | 4717–4697 |

This resulted in a +/−2000 bp DNA fragment that encompasses a relevant part of the transforming DNA (barnase, PTA29).

After purification, the DNA fragment was labeled according to standard procedures, and used for hybridizing to the membrane.

Hybridization was performed under standard stringency conditions: The labeled probe was denaturated by heating for 5 to 10 minutes in a water bath at 95° C. to 100° C. and chilling on ice for 5 to 10 minutes and added to the hybridization solution (6×SSC (20×SSC is 3.0 M NaCl, 0.3 M Na citrate, pH 7.0), 5×Denhardt's (100×Denhardt's=2% Ficoll, 2% Polyvinyl pyrollidone, 2% Bovine Serum Albumin), 0.5 % SDS and 20 μg/ml denatured carrier DNA (single-stranded fish sperm DNA, with an average length of 120–3000 nucleotides). The hybridization was performed overnight at 65° C. The blots were washed three times for 20 to 40 minutes at 65° C., with the wash solution (2×SSC, 0.1 % SDS).

The autoradiographs were electronically scanned.

Figure 4:
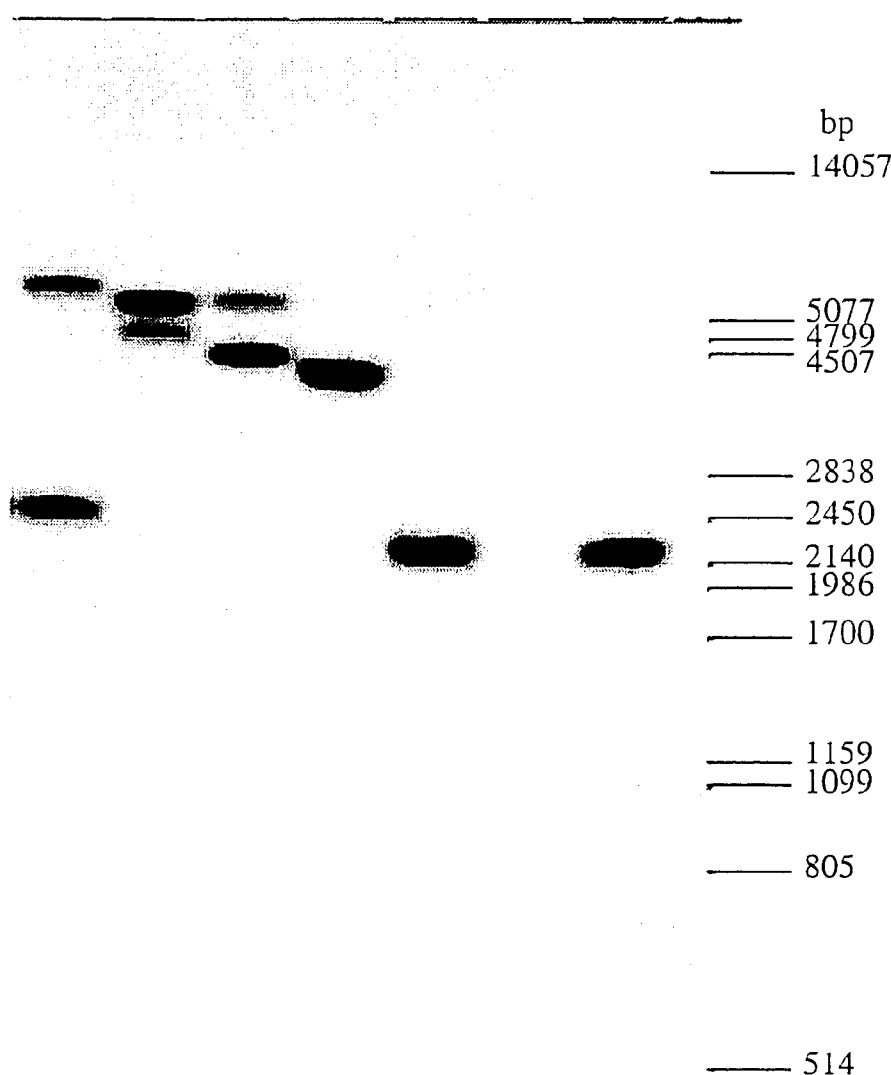
FIG. 4. Restriction map obtained after digestion of MS-B2 genomic DNA. Loading sequence of the gel analyzed by Southern blot: lane 1, MS-B2 DNA digested with NcoI, lane 2, MS-B2 DNA digested with EcoRV, lane 3, MS-B2 DNA digested with MunI, lane 4, MS-B2 DNA digested with HindIII, lane 5, MS-B2 DNA digested with EcoRI, lane 6, non-transgenic *Brassica napus* DNA digested with EcoRI, lane 7, non-transgenic *B. napus* DNA digested with EcoRI+control plasmid pTCO113 DNA digested with EcoRI, lane 8, Molecular weight marker (λ-PstI).

The restriction patterns obtained after digestion of MS-B2 genomic DNA with different restriction enzymes is presented in FIG. 4 and summarized in Table 2.

TABLE 2

Restriction map of MS-B2

| Lane number | DNA loaded | Migration of hybridizing DNA fragments between size marker bands | | Estimated length of the hybridizing DNA fragments. |
|---|---|---|---|---|
| | | Larger than | Smaller than | |
| 1 | MS-B2 - NcoI | 5077 | 14057 | 6000 bp |
| | | 2450 | 2838 | 2500 bp |
| 2 | MS-B2 - EcoRV | 5077 | 14057 | 5500 bp |
| | | 4507 | 5077 | 4800 bp |
| 4 | MS-B2 - MunI | 5077 | 14057 | 5700 bp |
| | | 2838 | 4799 | 4500 bp |
| 5 | MS-B2 - HindIII | 2838 | 4570 | 3938 bp (*) |
| 6 | MS-B2 - EcoRI | 1989 | 2450 | 2262 bp (*) |
| 7 | Non-transgenic Brassica | — | — | — |
| 8 | Control plasmid DNA - EcoRI | 1989 | 2450 | 2262 bp (*) |

(*) the lengths of these fragments are those predicted from the restriction map of the plasmid pTCO113

3.2 Identification of the Flanking Regions

The sequence of the regions flanking the inserted foreign DNA in the MS-B2 event was determined using the thermal asymmetric interlaced (TAIL-) PCR method described by Liu et al. (1995, The Plant Journal 8(3):457–463). This method utilizes three nested primers in successive reactions together with a shorter arbitrary degenerate primer so that the relative amplification efficiencies of specific and non-specific products can be thermally controlled. The specific primers were selected for annealing to the border of the foreign DNA and based on their annealing conditions. A small amount (5 μl) of unpurified secondary and tertiary PCR products were analyzed on a 1% agarose gel. The tertiary PCR product was used for preparative amplification, purified and sequenced on an automated sequencer using the DyeDeoxy Terminator cycle kit.

3.2.1. Right (5') Flanking Region

The primers used were:

| | Sequence (5'→3') | Position in pTCO113 |
|---|---|---|
| Degenerate primer MDB285 | NTC.gAS.TWT.SgW.gTT (SEQ ID No. 4) | — |
| Primary TAIL MDB251 | ggA.TCC.CCC.gAT.gAg.CTA.AgC.TAg.C (SEQ ID No. 5) | 293–317 |

-continued

| | Sequence (5'→3') | Position in pTCO113 |
|---|---|---|
| Secondary TAIL MDB193 | TCA.TCT.ACg.gCA.ATg.TAC.CAg.C (SEQ ID NO. 6) | 226–247 |
| Tertiary TAIL MDB258 | CTA.Cgg.CAA.TgT.ACC.AgC.Tg (SEQ ID No. 7) | 224–243 |

Whereby: N = A,C,T or g;S = C or g; W = A or T

The fragment amplified using MDB285-MDB258 was ca. 415 bp, the complete sequence of which was determined (SEQ ID No. 8). The sequence between nucleotide I and 234 corresponds to plant DNA, while the sequence between nucleotide 235 and 415 corresponds to T-DNA.

3.2.2. Left (3') Flanking Region

The primers used were:

| | Sequence (5'→3') | Position in pTCO113 |
|---|---|---|
| Degenerate primer MDB285 | NTC.gAS.TWT.SgW.gTT (SEQ ID No. 4) | — |
| Primary TAIL MDB8 | TCA.gAA.gTA.TCA.gCg.ACC.TCC.ACC (SEQ ID No 9) | 5249–5272 |
| Secondary TAIL MDB251 | ggA.TCC.CCC.gAT.gAg.CTA.AgC.TAg.C (SEQ ID NO. 5) | 5547–5572 |
| Tertiary TAIL MDB258 | CTA.Cgg.CAA.TgT.ACC.AgC.Tg (SEQ ID No. 7) | 5621–5640 |

Whereby: N = A,C,T or g;S = C or g: W = A or T

The fragment amplified using MDB285-MDB258 was ca. 416 bp, the complete sequence of which was determined (SEQ ID No. 10). The sequence between nucleotide 1 and 193 corresponds to T-DNA, while the sequence between nucleotide 194 and 416 corresponds to plant DNA.

3.3. Genetic Analysis of the Locus

The genetic stability of the insert for the MS-B2 event was checked by molecular and phenotypic analysis in the progeny plants over several generations.

Southern blot analyses of plants of the $T_0$, $T_1$ and $T_2$ generation were compared for the MS-B2 event. The patterns obtained were found to be identical in the different generations. This proves that the molecular configuration of the foreign DNA in MS-B2 was stable.

The MS-B2 event displayed Mendelian segregation for the transgenes as a single genetic locus in at least three subsequent generations indicating that the insert is stable.

On the basis of the above results MS-B2 was identified as an elite event.

Example 4

Introduction of MS-B2 Into *Brassica juncea, Brassica napus* WOSR and *Brassica rapa*

By molecular mapping it was determined that event MS-B2 is localized on the A genome of *Brassica napus*.

Event MS-B2 was introduced, by repeated backcrossing, from Drakkar variety plants comprising event MS-B2 into a *Brassica juncea* cultivar. After at least 6 generations of backcrosses, the *B. juncea* plants were examined and it was established that:

a) the presence of the foreign DNA did not compromise other desired characteristics of the plant, such as those relating to agronomic performance or commercial value;
b) the event was characterized by a well defined molecular configuration which was stably inherited;
c) the gene(s) of interest in the foreign DNA showed a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use;

Furthermore, the plants were evaluated for their agronomical characteristics and performance as compared with wild-type *Brassica juncea* species.

Extensive testing in the field demonstrated that MS-B2 in *Brassica juncea* resulted in plants which showed adequate expression of the genes of interest in the foreign DNA, i.e. a male-sterile phenotype, combined with optimal agronomic performance. Thus, although originally developed in a *B. napus,* it was surprisingly found that MS-B2 was also an elite event in *Brassica juncea*.

Event MS-B2 was introduced, by repeated backcrossing, from Drakkar variety plants comprising event MS-B2 into a *Brassica napus* winter oilseed rape. After at least 6 generations of backcrosses, the WOSR plants were examined and it was established that:

a) the presence of the foreign DNA did not compromise other desired characteristics of the plant, such as those relating to agronomic performance or commercial value;
b) the event was characterized by a well defined molecular configuration which was stably inherited;
c) the gene(s) of interest in the foreign DNA showed a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use;

Furthermore, the plants were evaluated for their agronomical characteristics and performance as compared with wild-type WOSR cultivars.

Extensive testing in the field demonstrates that MS-B2 in WOSR results in a plant which showed adequate expression of the transgenes in the foreign DNA, i.e. a male-sterile phenotype, combined with optimal agronomic performance. Thus, although originally developed in spring OSR, it was surprisingly found that MS-B2 was also an elite event in winter oilseed rape.

It was also found that MS-B2 can be introduced into *Brassica rapa* and that it is an elite event in this Brassica species. It can be concluded that, surprisingly, MS-B2 is an elite event in three different Brassica species, *B. napus, B. juncea* and *B. rapa*.

Example 5

Development of Diagnostic Tools for Identity Control

The following protocols were developed to identify any Brassica plant material comprising the elite event MS-B2.

5.1. MS-B2 Elite Event Restriction Map Identification Protocol

*Brassica napus* or juncea plants containing the elite event MS-B2 can be identified by Southern blotting using essentially the same procedure as described in Example 3.1. Thus Brassica genomic DNA is 1) digested with at least two, preferably at least 3, particularly with at least 4, more particularly with all of the following restriction enzymes: NcoI, EcoRV, MunI, HindIII, EcoRI, 2) transferred to nylon membranes and 3) hybridized with the a fragment of about 2000 bp generated by PCR amplification from the plasmid pTCO113 with primers MDB355 (SEQ ID No. 2) and MDB008 (SEQ ID No. 3) (as described in Example 3.1). If, with respect to at least two of the restriction enzymes used, DNA fragments are identified with the same length as those listed in Table 2, the Brassica plant is determined to harbor elite event MS-B2.

5.2. MS-B2 Elite Event Polymerase Chain Reaction Identification Protocol

A test run, with all appropriate controls, has to be performed before attempting to screen unknowns. The presented protocol might require optimization for components that may differ between labs (template DNA preparation, Taq DNA polymerase, quality of the primers, dNTP's, thermocyler, etc.).

Amplification of the endogenous sequence plays a key role in the protocol. One has to attain PCR and thermocycling conditions that amplify equimolar quantities of both the endogenous and transgenic sequence in a known transgenic genomic DNA template. Whenever the targeted endogenous fragment is not amplified or whenever the targeted sequences are not amplified with the same ethidium bromide staining intensities, as judged by agarose gel electrophoresis, optimization of the PCR conditions may be required.

5.2.1. Template DNA

Template DNA is prepared from a leaf punch or a single seed according to Edwards et al. (Nucleic Acid Research, 19, p1349, 1991). When using DNA prepared with other methods, a test run utilizing different amounts of template should be done. Usually 50 ng of genomic template DNA yields the best results.

5.2.2. Assigned Positive and Negative Controls

The following positive and negative controls should be included in a PCR run:

Master Mix control (DNA negative control). This is a PCR in which no DNA is added to the reaction. When the expected result, no PCR products, is observed this indicates that the PCR cocktail was not contaminated with target DNA.

A DNA positive control (genomic DNA sample known to contain the transgenic sequences). Successful amplification of this positive control demonstrates that the PCR was run under conditions which allow for the amplification of target sequences.

A wildtype DNA control. This is a PCR in which the template DNA provided is genomic DNA prepared from a non-transgenic plant. When the expected result, no amplification of a transgene PCR product but amplification of the endogenous PCR product, is observed this indicates that there is no detectable transgene background amplification in a genomic DNA sample.

5.2.3. Primers

The following primers, which specifically recognize the foreign DNA and a flanking sequence of MS-B2 are used:
B01: 5'-gAA.ATC.CAT.gTA.AAg.CAg.CAg.gg-3' (SEQ ID 11)
(MDB371) (target: plant DNA)
B02: 5'-gCT.Tgg.ACT.ATA.ATA.CTT.gAC-3' (SEQ ID 12)
(MDB201) (target: T-DNA)

Primers targeting an endogenous sequence are always included in the PCR cocktail. These primers serve as an internal control in unknown samples and in the DNA positive control. A positive result with the endogenous primer-pair demonstrates that there is ample DNA of adequate quality in the genomic DNA preparation for a PCR product to be generated. The endogenous primers used are:
B03: 5'-AAC.gAg.TgT.CAg.CTA.gAC.CAg.C-3' (SEQ ID 13)
(CVZ7) (located in *B. napus* cruA gene (X1455))
B04: 5'-CgC.AgT.TCT.gTg.AAC.ATC.gAC.C-3' (SEQ ID 14)
(CVZ8) (located in *B. napus* cruA gene (X1455))

5.2.4. Amplified Fragments

The expected amplified fragments in the PCR reaction are:
For primer pair B03-B04: 394bp (endogenous control)
For primer pair B01-B02: 183bp (MS-B2 Elite Event)

5.2.5. PCR Conditions

The PCR mix for 25 $\mu$l reactions contains:

2.5 $\mu$l template DNA 2.5 $\mu$l 10×Amplification Buffer (supplied with Taq polymerase)

0.5 $\mu$l 10 mM dNTP's 0.5 $\mu$l B01 (10 pmoles/$\mu$l)

0.5 $\mu$l B02 (10 pmoles/$\mu$l)

0.25 $\mu$l B03 (10 pmoles/$\mu$l)

0.25 $\mu$l B04 (10 pmoles/$\mu$l)

0.1 $\mu$l Taq DNA polymerase (5 units/$\mu$l)

water up to 25 $\mu$l

The thermocycling profile to be followed for optimal results is the following:

4 min. at 95° C.

Followed by: 1 min. at 95° C.
    1 min. at 57° C.
    2 min. at 72° C.
    For 5 cycles Followed by:
    30 sec. at 92° C.
    30 sec. at 57° C.
    1 min. at 72° C.
    For 25 cycles Followed by:
    5 minutes at 72° C.

5.2.6. Agarose Gel Analysis

Between 10 and 20 µl of the PCR samples should be applied on a 1.5% agarose gel (Tris-borate buffer) with an appropriate molecular weight marker (e.g. 100 bp ladder PHARMACIA).

5.2.7. Validation of the Results

Data from transgenic plant DNA samples within a single PCR run and a single PCR cocktail should not be acceptable unless 1) the DNA positive control shows the expected PCR products (transgenic and endogenous fragments), 2) the DNA negative control is negative for PCR amplification (no fragments) and 3) the wild-type DNA control shows the expected result (endogenous fragment amplification).

Lanes showing visible amounts of the transgenic and endogenous PCR products of the expected sizes, indicate that the corresponding plant from which the genomic template DNA was prepared, has inherited the MS-B2 elite event. Lanes not showing visible amounts of the transgenic PCR products and showing visible amounts of the endogenous PCR product, indicate that the corresponding plant from which the genomic template DNA was prepared, does not comprise the elite event. Lanes not showing visible amounts of the endogenous and transgenic PCR products, indicate that the quality and/or quantity of the genomic DNA didn't allow for a PCR product to be generated. These plants cannot be scored. The genomic DNA preparation should be repeated and a new PCR run, with the appropriate controls, has to be performed.

5.2.8. Use of Discriminating PCR Protocol to Identify MS-B2

Brassica leaf material from plants comprising MS-B2 or another transgenic event were tested according to the above-described protocol. Samples from *Brassica napus* wild-type were taken as negative controls.

Figure 5:
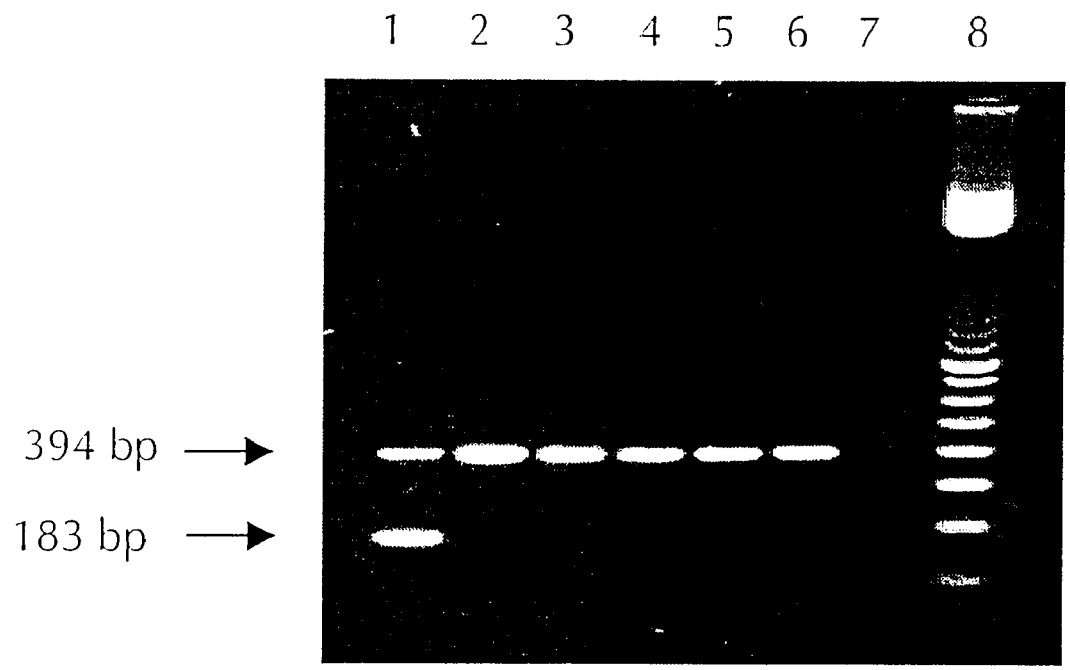
FIG. 5. PCR analysis of other events and elite event MS-B2 using the MS-B2 PCR identification protocol. Loading sequence of the gel: lane 1, DNA sample from a Brassica plant comprising the transgenic event MS-B2, lane 2–5, DNA samples from Brassica plants comprising other transgenic events, lane 6, DNA from wild-type Brassica, lane 7, negative control (water), lane 8, molecular weight marker (100 bp ladder).

FIG. 5 illustrates the result obtained with the elite event PCR identification protocol for MS-B2 on a number of Brassica samples (lanes 1 to 5). The sample in lane 1 is recognized to contain the elite event as the 183 bp band is detected, while the samples in lanes 2 to 5 do not comprise MS-B2. Lane 6 represents a non-transgenic Brassica control, and lane 7 the negative control (water) sample.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts.

Seed comprising elite event MS-B2 was deposited at the American Tissue Culture Collection under accession number: PTA-850.

The above description of the invention is intended to be illustrative and not limiting. Various changes or modifications in the embodiments described may occur to those skilled in the art. These can be made without departing from the spirit or scope of the invention.

We claim:

1. A transgenic male sterile and glufosinate resistant Brassica plant, or seed, cell or tissue thereof, wherein the genomic DNA of said plant, or seed, cell or tissue comprises MS-B2 elite event and yields a DNA fragment of between 160 and 200 bp, in the MS-B2 Elite Event Polymerase Chain Reaction Identification Protocol.

2. The transgenic Brassica plant, or seed, cell or tissue thereof, according to claim 1, wherein the genomic DNA of said plant, or seed, cell or tissue yields, when analyzed according to the MS-B2 Elite Event Restriction Map Identification Protocol, at least two of the restriction fragments or sets of restriction fragments selected from the group consisting of:
  i) one set of NcoI fragments, one with a length of between 5077 and 14057 bp, and one with a length of between 2450 and 2838 bp;
  ii) one set of EcoRV fragments, one with a length of between 5077 and 14057 bp, and one with a length of between 4507 and 5077 bp;

iii) one set of MunI fragments, one with a length of between 5077 and 14057 bp, and one with a length of between 2838 and 4799 bp;

iv) one HindIII fragment with a length of between 2838 and 4507 bp; and v) one EcoRI fragment with a length of between 1989 and 2450 bp;

wherein each of the restriction fragments is capable of hybridizing, under standard stringency conditions, with the +/−2000 bp fragment obtainable by PCR amplification of a fragment of SEQ ID No. 1, using the probes having the nucleotide sequence of SEQ ID No. 2 and SEQ ID No. 3 respectively.

3. The Brassica plant, or seed, cell or tissue thereof, according to claim 2, wherein the genomic DNA of said plant, or seed, cell or tissue yields, in the MS-B2 Elite Event Restriction Map Identification Protocol, at least three restriction fragments or sets of restriction fragments selected from said group.

4. The Brassica plant, or seed, cell or tissue thereof, according to claim 3, wherein the genomic DNA of said plant, or seed, cell or tissue yields, in the MS-B2 Elite Event Restriction Map Identification Protocol, at least four restriction fragments or sets of restriction fragments selected from said group.

5. The Brassica plant, or seed, cell or tissue thereof, according to claim 4, wherein the genomic DNA of said plant, or seed, cell or tissue yields, in the MS-B2 Elite Event Restriction Map Identification Protocol, all five restriction fragments or sets of restriction fragments selected from said group.

6. The Brassica plant, or seed, cell or tissue thereof, according to claim 1, wherein a DNA fragment of about 183 bp, is amplified from the genomic DNA of said plant, or seed, cell or tissue in the MS-B2 Elite Event Polymerase Chain Reaction Identification Protocol.

7. The Brassica plant, or seed, cell or tissue thereof, according to claim 1, which is grown from the Brassica seed deposited at the ATCC under accession number PTA-850.

8. A Brassica plant, or seed, cell or tissue thereof, obtained by propagation of, and/or breeding with, a Brassica plant grown or derived from a Brassica seed deposited at the ATCC under accession number PTA-850, wherein the genomic DNA of said plant, or seed, cell or tissue comprises elite event MS-B2 and yields a DNA fragment of between 160 and 200 bp, in the MS-B2 Elite Event Polymerase Chain Reaction Identification Protocol.

9. A method for identifying a transgenic male sterile and glufosinate resistant Brassica plant, or cell or tissue thereof, comprising the elite event MS-B2, wherein the method comprises establishing whether the genomic DNA of said plant or cell or tissue yields a DNA fragment of between 160 and 200 bp, under the conditions of the MS-B2 Elite Event Polymerase Chain Reaction Identification Protocol, in which two primers having the nucleotide sequences of SEQ ID No. 11 and SEQ ID No. 12, respectively, are used.

10. The method of claim 9, wherein the DNA fragment is about 183 bp.

11. The Brassica seed deposited at the ATCC under accession number PTA-850.

12. A process for producing hybrid seed, which process comprises crossing the male-sterile Brassica plant of claim 1, with a male-fertile Brassica plant, and harvesting hybrid seed from said male-sterile plant.

13. A Brassica plant, or cell, tissue or progeny thereof grown from the seed as claimed in claim 11, wherein the plant or cell, tissue or progeny each comprise elite event MS-B2.

14. A transgenic Brassica plant or seed thereof, each comprising elite event MS-B2, seed comprising said elite event MS-B2 having been deposited as ATCC Accession number PTA-850.

15. A transgenic Brassica seed comprising elite event MS-B2, reference seed comprising said elite event MS-B2 having been deposited as ATCC accession number PTA-850.

16. A Brassica seed or plant comprising elite event MS-B2 and obtained from crossing the plant of claim 1 with a male fertile Brassica plant.

17. A method for identifying the seed or plant of claim 16, wherein the method comprises establishing whether the genomic DNA of said plant yields a DNA fragment of between 160 and 200 bp, under the conditions of the MS-B2 Elite Event Polymerase Chain Reaction Identification Protocol, in which two primers having the nucleotide sequences of SEQ ID No. 11 and SEQ ID No. 12, respectively, are used.

* * * * *